United States Patent [19]

Hagmann et al.

[11] Patent Number: 4,897,600
[45] Date of Patent: Jan. 30, 1990

[54] HIGH FREQUENCY AMMETER

[75] Inventors: Mark J. Hagmann, Miami; Tadeusz M. Babij, Fort Lauderdale, both of Fla.

[73] Assignee: Florida International University, Miami, Fla.

[21] Appl. No.: 122,201

[22] Filed: Nov. 13, 1987

[51] Int. Cl.$^4$ .......................... G01R 1/22; H01F 15/04
[52] U.S. Cl. ...................................... 324/127; 324/95; 324/117 R; 336/84 C
[58] Field of Search ...................... 324/127, 117 R, 95, 324/106; 336/84 C, 84 R, 84 M

[56] References Cited

U.S. PATENT DOCUMENTS

| | | | |
|---|---|---|---|
| 3,434,052 | 3/1969 | Fechant | 324/127 |
| 3,721,900 | 3/1973 | Andrews | 324/95 |
| 3,794,914 | 2/1974 | Aslan | 324/95 |
| 3,885,213 | 5/1975 | Rioux et al. | 324/117 R |
| 3,931,573 | 1/1976 | Hopfer | 324/95 |
| 4,207,518 | 6/1980 | Hopfer | 324/95 |

FOREIGN PATENT DOCUMENTS 2538908 7/1984 France .................. 324/158 MG
954559 4/1964 United Kingdom ................. 324/95

Primary Examiner—Ernest F. Karlsen
Attorney, Agent, or Firm—Harry W. Barron

[57] ABSTRACT

A current detector for detecting the high frequency current flowing in a conductor includes a coil of high resistivity material wound around an non-ferromagnetic core. The coil is arranged in a substantially closed loop configuration around the conductor carrying the current to be measured. The ratio of the winding spacing to the cross sectional area of the coil is maintained constant over the length of the winding. A shield of high resistivity material surrounds the coil and is spaced from the coils and the shield has a gap oriented along an azimuth of the closed loop winding and directed orthogonal to the net current direction of the current induced in the coil. The ends of the coil are coupled to a high impedance voltage detector through high resistivity leads and a relatively low value resistor is coupled between the leads to reduce the quality factor. The current detector may be used to detect current flowing in a human body due to the absorption of high frequency incident radiation as an indication of the specific absorption rate of such radiation.

13 Claims, 1 Drawing Sheet

HIGH FREQUENCY AMMETER

This invention relates to apparatus for detecting a high frequency current in a conductor, and more particularly to such apparatus which is placed around the conductor and uses the magnetic field produced by the high frequency current to measure the current without perturbing the ambient electric and magnetic fields.

There is increasing concern regarding the hazards which may result from exposure of humans to electromagnetic energy. A large number of electromagnetic radiators, including radio and television stations, radar transmitters, microwave ovens, and communications equipment, contribute to the total exposure of humans to non-ionizing radiation. In addition, some industrial workers are exposed to the fields from such devices as radio frequency heat sealers and inductive heaters. Exposure to the field of EHV lines used for power transmission is also becoming more common. The National Institute for Occupational Safety and Health (NIOSH) and the American National Standards Institute (ANSI) have both been involved in attempting to define safety criteria.

Considerable effort is being spent in both experiments with animal models and theoretical analysis to examine the biological effects of non-ionizing electromagnetic energy. An important part of this work is dosimetry, that is determining the amount of energy absorbed under various conditions. Dosimetry is much more difficult for nonionizing electromagnetic energy than it is for ionizing radiation because, unlike ionizing radiation, the absorbed dose is not simply related to the incident flux. The absorption of electromagnetic energy is dependent upon the dimensions, composition and posture of the body, as well as the frequency, polarization, and other properties of the radiations. Generally the most intense exposure occurs under near-field conditions, where the electric and magnetic fields are not simply related and where it is often difficult to accurately characterize the source.

There is a strong need for a non-invasive personal dosimeter for electromagnetic energy corresponding to the devices that are in general use with ionizing radiation; however, no suitable non-invasive device has thus far been suggested. Dosimetry for electromagnetic energy has been limited to invasive measurements of the temperature or fields within laboratory animals and models of man, as well as to computer simulations. The fields external to the body are a superposition of incident and scattered waves, so that measurements made close to the body generally fail to permit accurate characterization of either the external fields or those of the incident wave. For this reason, it has generally been impossible to make meaningful predictions of the absorbed dose from non-invasive measurements.

More specifically, there is also considerable need for a device which would quantify the dose received by a patient when electromagnetic energy is used for therapeutic purposes, such as diathermy and the hyperthermic treatment of cancer. Hyperthermia has shown considerable promise for the adjuvant treatment of cancer, but there has been difficulty in treating deep-seated tumors with the required degree of precision. Computer simulations and clinical observations suggest that considerable aberrant heating may occur in hyperthermia due to deposition of energy outside the region intended for treatment. At present, it is only possible to monitor the temperature at a few intracavity or interstitial locations, so that the physician must rely on the complaints of pain from the patient for guidance during treatment. However, heating at locations in the core of the body is often perceived as a dull pressure, so patient complaints are difficult to interpret, but significant damage can still occur.

Ampere's Law states that the line integral of the magnetic field intensity around the closed path is equal to the total electric current passing through the region enclosed by the path.

$$\oint \vec{H} \cdot \vec{dl} = I \tag{1}$$

A ferromagnetic core having cross-sectional area A and permeability $\mu$, may be formed to make a closed loop of length L. If the core has a high permeability, the flux within the core at any part of the loop is related to the current passing through the aperture enclosed by the loop, according to the following equation:

$$\Phi = \mu AI/L \tag{2}$$

A coil consisting of N turns may be wound around the core at any location on the loop and the potential induced on the coil is given by the equation:

$$V = -jw\mu NAI/L \tag{3}$$

where time dependence of $e^{jwt}$ is assumed.

Equation 3 can be used to determine the current I from the potential V measured across the coil. This principle has been used in clamp-on ammeter instruments for many years. These devices allow the measurement of a.c. current in power circuits without cutting the lines and interrupting service. Current probes are also commercially available, which serve as transducers to be used with separate meters, oscilloscopes, or other measuring instruments. These probes have either a clamp-on design, which opens for placement around the conductor, or a fixed configuration which requires that the conductor be passed through the central aperture.

At the present time, no device is available for use as a non-invasive dosimeter for electromagnetic energy. In prior studies, measurements were made of the fields external to the body and it was concluded that such measurements were not suitable for predicting the internal fields. Other studies have shown that electric field probes located near the body have a response that is strongly dependent on a number of factors, including the distance between the probe and the body. For example, see Misra et al "Response of Electric Field Probes Near A Cylindrical Model of the Human Body", *IEEE Transaction on Microwave Theory and Techniques, Vol. MTT* 33, pages 447-452 (June 1985). These studies confirmed that simple field measurements made external to the body have little or no value in dosimetry.

Others have recommended that, when the BSD Annular Phased Array manufactured by BSD Medical Corp. of Salt Lake City, Utah is used to induce hyperthermia, non-invasive electric field probes be used to measure the axial electric field at several locations near the surface of the body, particularly beneath the applicator. Measurements made with these probes are used in adjusting the applicator, and it is inferred that such measurements relate to the fields within the body. Since the Annular Phased Array produces an electric field that is predominantly axial in orientation at the locations where the measurements are made, boundary relations suggest that the electric field intensity immediately inside the body would be approximately equal to that measured near the surface. However, such measurements do not accurately reflect the total (axial) current distribution over the cross section of the body; rather they are limited to currents near the surface.

Active microwave imaging methods have also been used to obtain approximate images of inhomogeneous dielectric objects. For example, see Pichot et al "Active Microwave Imaging of Inhomogeneous Bodies", *IEEE Transactions on Antennas and Propagation*, Vol. AP-33 pages 416-425 (April 1985). Related methods could be used to determine the distribution of current within the body from non-invasive measurements. Other procedures based on moment method calculations, have also been considered for use in non-invasive measurements of the human body, and results of mathematical modeling suggest that it would be possible to use them to determine the specific absorption rate (SAR) of energy disposition. Each of these methods is quite complex, requiring computations based upon accurate measurements with special purpose probes. They do not appear suitable for use as a personal dosimeter at the present time.

In the patent literature, others have attempted to use various techniques to measure the interaction of radiation with the human body. For example, in U.S. Pat. No. 3,639,841 to Richardson, a circuit was provided for measuring the field strength near the body. However, such measurements are not suitable for predicting the currents induced within the body. Other patents in which radiation has been measured include U.S. Pat. No. 3,277,300 to Kerr et al in which a photovoltaic cell is used to detect infrared radiation; U.S. Pat. No. 3,878,496 to Erickson, in which a Geiger-Mueller tube is used to detect ionizing radiation; and U.S. Pat. No. 4,196,425 to Williams Jr. et al, in which the activity of the patient is monitored by detecting a interruption of an infrared beam passing above the area of confinement. Other patents in which radiation is detected include; U.S. Pat. No. 4,199,716 to Reindel for a hand held receiver and antenna used to indicate the presence of microwave radiation from microwave ovens or other microwave sources; U.S. Pat. No. 4,229,733 to Tulenko et al using a solar cell to detect ultra-violet radiation; and U.S. Pat. No. 4,338,595 to Newman describing a device suitable for detection of microwave energy emitted by microwave ovens or other microwave devices. These last three patents, in particular, have virtually no use in measuring the amount of energy absorbed by a object, such as a human body which is a lossey dielectric object.

It is also well known that current can be determined from measurements of the magnetic field surrounding the object carrying the current. Well known examples of devices for determining current based upon a magnetic field measurement include clamp-on ammeters, which typically include an iron core which is adapted to being placed around the conductor. The magnetic field surrounding the conductor will then flow through the magnetic core of the clamp-on ammeter and can be detected by placing a winding at a convenient location around the core. Patents literature illustrating this techniques include U.S. Pat. Nos. 2,802,182 to Godshalk et al 3,984,798 to Bussen, 4,456,873 to Schweitzer and U.S. Pat. No. 3,323,056 to Haley.

As will be discussed hereafter, it is preferable, when measuring high frequency currents through a conductor, to utilize a non-ferrogmagnetic core with high resistivity; air is an excellent example of such a core. Many prior patents have discussed utilizing nonmagnetic cores, including air cores, for various purposes. They include U.S. Pat. Nos. 3,434,052 to Fechant; 3,652,935 to Shaw; 4,348,638 to Boldridge; 4,581,598 to York; and 4,621,231 to Heinrich et al. However, none of the structures described in the aforementioned patents are satisfactory for measuring the current flowing through the conductors, such as an animal body because they perturb the surrounding fields due to the low resistance coil.

In accordance with one aspect of this invention, there is provided a current detector for detecting high frequency currents flowing through an object including a high resistivity conductor wound in multiple turns around a substantially closed loop non-ferrogmagnetic core. The loop has an aperture greater than the corresponding dimensions of the object to be measured and at any given point along the loop, the ratio of the turns spacing to the core cross-sectional area at the point is constant.

One preferred embodiment of the subject invention is hereafter described, with specific reference being made to the following Figures, in which.

Figure 1:
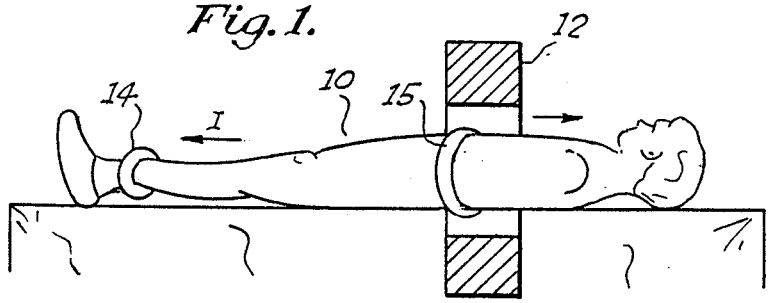
FIG. 1 shows a patient undergoing a hyperthermic treatment for cancer.

As previously discussed, it has been long known that it is possible to measure the current through a conductor by surrounding the conductor with a magnetic core having windings around the core. It also is possible to determine the current from non-invasive measurements without using a ferromagnetic core. A solenoidal winding having N uniformly spaced turns with cross-sectional area A may be formed into a closed loop of length L. If the coil is formed around a non-ferromagnetic core, such as air (permeability $\mu_0$), then the flux within the core at any point along the coil is given by $$\Phi = \mu_0 A \vec{H} \cdot \hat{l} \tag{4}$$

The potential induced in this coil is then $$V = -(jw\mu_0 NA/L) \oint \vec{H} \cdot \vec{dl} \tag{5}$$

Using Ampere's law, the potential is $$V = -jw\mu_0 NAI/L \tag{6}$$

Equation (6) may be used to determine the current I from the potential V measured across the coil. The difference between this procedure and the procedure described above with respect to equation (3) is that a ferromagnetic core is not required. However, the ratio of the wire spacing between turns to the core cross sectioned 1 area must be constant over the length of the coil when equation (6) is used. Conventional clamp-on ammeter instruments utilized a ferromagnetic core, and low resistance windings, thereby disturbing the ambient electric and magnetic fields. Where one is measuring a current induced in an object by an external field, the disturbance of the field effects the current being measured, thereby making the results incorrect. In the present invention, the use of non-ferromagnetic core, together with high resistance windings, does not disturb the ambient field, and thus, the present invention is useful to measure a current induced by an electromagnetic field.

Since the electromagnetic fields of interest are time dependent, personal dosimeter devices based on either equation (3) or equation (6) must respond to displacement current, as well as conduction current. Thus, it is expected that there will be a reading due to the surrounding environment, even without the body or other object being inserted in the device aperture. When the body or other object is present and the fields are axially polarized, a sizeable space may still exist in the aperture between the coil and the body without introducing appreciable errors due to displacement currents in the aperture. Since the magnitudes of the electric field intensity inside and outside the body are comparable, and the magnitude of the relative permittivity of muscle and other body tissues having a high water content is large, the current density within the body is much greater than the displacement current density in air. Furthermore, since the imaginary component of the relative permittivity of the body tissue is dominant, the measured value of the current is directly related to the energy deposited in the tissues.

Low-frequency approximations are implicit in both of the derivations presented in this section. If the length of the loop (L) is not much smaller than a wavelength within the contained medium, it is necessary to correct for both retarded times and attenuation during propagation to the coil. These effects cause a decrease in the output from the coil. Table I shows calculated values illustrating the effect of propagation on the output of a torroid surrounding a cylinder of muscle having an axial current that is assumed constant over the cross section.

TABLE I

| | Radii of Muscle Cylinders (cm) for Specified Deviation of Coil Output from Equation (6) | | | | | |
|---|---|---|---|---|---|---|
| Percent | 1 | 10 | 27.12 | 50 | 80 | 150 | (Frequency in MHz) |
| −10 | 24 | 7 | 5 | 3 | 2 | 1.5 | |
| −20 | 49 | 14 | 9 | 7 | 5 | 3 | |
| −30 | — | 23 | 14 | 10 | 8 | 5 | (radii in cm) |
| −40 | — | 32 | 21 | 14 | 11 | 7 | |
| −50 | — | — | 28 | 20 | 14 | 9 | |

At frequencies used in AM broadcasting (about 1 MHz), the value from equation (6) have errors less than 10 percent for cylinders having radii as large as the human torso (24 cm radius). At 27.12 MHz, commonly used with RF heat sealers and other commercial devices, errors of less than 20 percent would be found with cylinders having radii as large as the thigh (9 cm). At the higher frequencies (>80 MHz) used in hyperthermia, the deviation would be about 30 percent with a cylinder having a radius as large as the neck or limb.

Smaller errors are expected with measurements of the human body than with muscle cylinders having similar cross sections, since the attenuation in bone and fat is substantially less than that in muscle. The effects of propagation, which limit the accuracy of equation (6), also limit the depth of deposition of electromagnetic energy in tissue. For this reason, the conditions under which sizeable errors would be found with equation (6) are those in which it would be unlikely that electromagnetic energy could cause significant heating.

The American National Standards Institute (ANSI) guide recommends that, for human exposure, the incident electric field (rms) should be limited as follows:

$E=632$ V/m from a Frequency $F=0.30$ MHz to 3.0 MHz.

$E=1897/F$ V/m for $F=3.0$ MHz to 30 MHz.

$E=61.4$ V/m for $F=30$ MHz to 300 MHz.

The ANSI committee used the results from experiments with laboratory animals and models of man, as well as computer simulations, to determine these limits for incident fields. The two expressions for frequencies above 3 MHz were designed to compensate for the frequency dependence of absorption, so that the rate of whole body energy absorption under various exposure conditions will not exceed a limit which they chose. At frequencies below 3 MHz, the limit was set primarily due to consideration of hazards from shock and burns.

Since a variety of exposure conditions is possible, it appears that the limits recommended by ANSI may be overly protective in some cases, but insufficiently strict in others. Uncertainty regarding the conditions of exposure required the ANSI committee to make the additional recommendations that the peak rate of energy deposition (specific absorption rate, or SAR, in watts per unit mass) should not exceed 8 W/kg for any one gram of tissue in the body. The equipment that is presently available would require the use of invasive measurements for enforcement of the latter recommendation.

The ANSI committee has not yet made recommendations for frequencies below 0.3 MHz, but it appears that the hazard from shock or burns at the lower frequencies is directly related to the electric current, rather than the SAR. The present invention appears especially appropriate for use at these lower frequencies because the measured parameter is electric current. Another possible application, of the present invention would be a personal dosimeter device that could be fabricated as a part of a belt to be affixed over the clothing of utility workers, in order to quantify the intensity of possible electrical shock. Values of the "let-go" current have been specified as safety criteria for use at power-line frequencies. Values of the SAR can be calculated from non-invasive measurements of current and published values for the dielectric properties of tissue. The ANSI recommended limit of peak SAR could be enforced if local values were approximated in this manner.

Referring now to FIG. 1, both modeling experiments and computer simulations have show that, when a person 10 is exposed to electromagnetic energy, such as from a high frequency applicator device 12, the energy absorbed by the body is greatest when the electric field vector is parallel to the length of the body; this is known as E-polarization. Experiments with mannequins and computer simulations have shown that with E-polarization, there is an electric current I that follows vertically through the body such that the current at one location is related to the current at other locations. The dosimeter 14 of the present invention may be used to determine the current I at a convenient location, such as a leg or an ankle. A larger dosimeter 15 may be attached around the area of a person 10 receiving treatment, such as the abdomen. Published values of the dielectric properties of tissue can be used with these measurements to determine the approximate SAR in the treated area, as well as other parts of the body.

Both computer simulation and modeling experiments have shown that an applicator 12 providing E-polarization, such as an Annular Phased Array or a helical coil, is more suitable for treating deep-seated tumors than are applicators having other polarizations. Computer simulations further suggest that the aberrant heating is most severe with E-polarization. Experiments using models of man have shown that the local SAR in the neck may be twice that in the abdomen when a Annular Phased Array applicator 12 is positioned for abdominal heating, as shown in FIG. 1. Significant aberrant heating has also been observed in experiments with the helical coil applicators.

At the present time, clinicians have no tool to measure aberrant deposition non-invasively. The dosimeter 14 of the present invention may be effectively used to determine the longitudinal flow of current I through various parts of the body, since it is insensitive to azimuthal or other circulating current. Since the aberrant heating during hyperthermia treatment is generally due to the axial flow of current in various narrow bodily regions (e.g. the neck, the arms, and legs), dosimeter 14 is useful as a tool for indicating such aberrant heating.

Certain industrial workers may be repeatedly exposed to hazardous electromagnetic fields as part of their duties. A personal dosimeter, such as dosimeter 14 in FIG. 1, may be used to determine and store the currents induced as a result of the exposure. Later the stored values may be retrieved and used to approximate the SAR throughout the body for that worker. If the approximate SAR exceeds a threshold, corrective action will be required. Local values of SAR determined for the leg or ankle are particularly of interest, since the peak value often occurs in these regions. Alternatively, several personal dosimeter devices 14 may be used at different parts of the body.

The principle of the present invention is related to that used in commercial clamp-on a.c. ammeters and current probes. However, these instruments have not been used in dosimetry and it appears that they do not satisfy some of the requirements which are essential for proper implementations of the present invention. The most significant difference between the present invention and the available devices is that the available devices all perturb the field which induce the current being measured, thereby rendering inaccurate any reading obtained. Another difference between the present invention end the prior art is that the present invention permits a significantly larger apertures so that the device can surround the body at the waist, or another location, instead of only enclosing a wire. Further, and particularly at high frequencies, the large size required for the winding of a conventional clamp-on ammeter can cause increased problems from self resonance of the device. These problems have been overcome in dosimeters 14 and 15 by reducing the Q-factor through loading. Another difference is that existing clamp-on ammeters require a ferromagnetic core, which should be avoided in order to reduce the weight of the dosimeter, as well as to avoid the errors caused by saturation and dependence of permeability on frequency. The use of ferromagnetic cores must further be limited to use with low frequencies, where the added gain from large relative permeability is desirable. Even in these applications, such as a shock-hazard monitor for utility workers, a dosimeter device should have low weight and be flexible and adjustable so that it can be incorporated and easily affixed around the body without undue discomfort.

Figures 2, 2A:
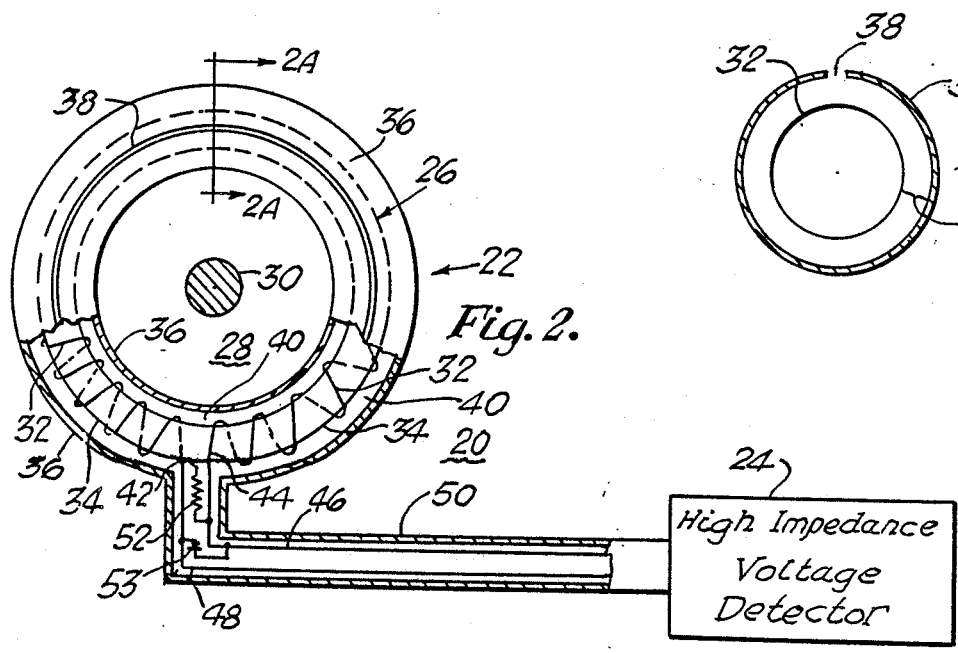
FIG. 2 shows a personal dosimeter device useful for measuring the current through the patient shown in FIG. 1.
FIG. 2A is a cross-section taken across lines 2A—2A of FIG. 2.

Referring now to FIG. 2, a personal dosimeter 20 including in a transducer 22 and a detector 24, is shown, which can measure the current I, shown in FIG. 1. The detector 24 may be any conventional high impedance voltage detector, and any digital readout or storage devices desirably attached thereto. Transducer 22 includes a coil 26 surrounding a central aperture 28 through which an object 30 passes. Object 30 may be a body limb or other conductor through which current passes.

Coil 26 is formed by winding a high resistance conductor 32 around a non-ferromagnetic material, such as air core 34. Because the air core 34 has a low permeability, at each point of coil 26 the ratio of the turn spacing between adjacent turns of conductor 32 and the cross-sectional area of air core 34, at that point, should be constant. This constant ratio of turn spacing to cross sectional area is desirably maintained over the entire length of coil 26. The reason for this is to permit equal sensitivity at any, position within aperture 28. In other words, object 30 may be positioned anywhere in aperture 28 and the same results will be obtained. The requirement for a constant turns spacing to area ratio is not necessary if a ferromagnetic core is used, because a constant flux is maintained at all points in the ferromagnetic core.

The core 34 must have a low permeability, such as air, in order to allow measurement of the induced high frequency currants normally associated with diathermy and hyperthermic treatments, so as not to perturb the inducing field. An air, or other flexible low permeability material, core further has the advantage that the coil 26 is flexible and can fit around the conductor 30 in an non-circular fashion. For example. where the person 10 in FIG. 1 is positioned on a examining table and the personal dosimeter 14 of FIG. 1 corresponds to dosimeter 20 of FIG. 2, the dosimeter 20 is positioned around the ankle area of the person. In this position, the coil 26 would tend to be more elliptical than circular. This is particularly advantageous so that the length of the coil 26 can be made greater than the circumference around the ankle, or other location of measurement, which vary substantially from patient to patient.

High resistivity conductor 32 should have a volume resistivity such that the ratio of the volume resistivity to the thickness or diameter of conductor is in the range of 1000 ohms to 1,000,000 ohms and preferable about 100,000 ohms. The material of conductor 32 may be, for example, carbon loaded Teflon or conductive rubber materials. The purpose for using a high resistivity conductor 32 is to prevent or inhibit the perturbance of any existing electric fields which are in the area. Ideally, the windings 32 over the air core 34 will only respond to the magnetic field from the conductor 30 in the aperture 28. This magnetic field will be generated due to the current I flowing through conductor 30, and as previously discussed, relates to the SAR from applicator 12. The high resistivity of the windings formed by conductor 32 also prevents false readings due to perturbance of the current inducing fields.

In order to prevent capacitive coupling between transducer 22 and object 30, an electrostatic shield 36 of a high resistivity material is wrapped around the coil 26. A gap 38 in shield 36 extends entirely along the closed loop of coil 26. The purpose of gap 38 is to permit only magnetic coupling through the shield. It may be one millimeter in width. Again, shield 36 may be made of carbon loaded Teflon material or conductive rubber material. The ratio of the volume resistively to the thickness of the material of shield 36 ideally should be 100,000 ohms, but may be within the range of 1,000 ohms to 1,000,000 ohms. The presence of shield 36 as well as the constant ratio of turns spacing to cross sectional area, previously discussed, permits object 30 to be positioned at any point within the aperture 28 of coil 26 and still obtain substantially the same reading.

In order for shield 36 to properly operate, a space 40 is left between the inner surface of shield 36 and the outer surface of the conductor 32 forming coil 26. The space 40 is required to reduce the self-capacitance of the coil 26, thereby increasing the sensitivity and frequency responses of device 22. A distance of between two and three millimeter may be used for space 40.

As current flows through object 30, it creates a magnetic field around object 30, including in the core 34 of coil 26. This magnetic field in the core 34 induces a voltage on each turn of coil 26. The total voltage across the two ends 42 and 44 of the high resistivity conductor 32 forming coil 26 as measured by high impedance voltage detector 24, in turn, manifests the current flowing in object 30. In order to maintain a uniform spacing between the turns of coil 26, the ends 42 and 44 of coil 26 should be positioned substantially adjacent to one another, separated only by a spacing equal to the normal turns spacing. This spacing is necessary in order to minimize the errors due to non-constant turns spacing to coil cross sectional area ratio, as discussed above. However, if care is utilized to maintain the ratio of turns spacing to cross sectional area constant throughout the remainder of coil 26, some error can be permitted at the junction of ends 42 and 44.

The leads extending from ends 42 and 44 of high resistivity material conductor 32 are coupled to the high impedance voltage detector 24 by high resistivity leads 46 and 48, which are also contained in a shield 50. By making leads 46 and 48 of a high resistivity material, such as carbon loaded Teflon or conductive rubber, and providing a similar high resistivity shield 50, the minimal disturbance of the ambient electromagnetic fields is maintained.

Device 22 includes inductance due to the winding of coil 26, capacitance due to the coupling of coil 26 to shield 36 and the coil 26 self capacitance and resistance from conductor 32, thereby creating and RLC resonant circuit. The sensitivity of device 22, as a result of this resonant circuit, is strongly dependent an frequency, unless the quality factor (Q) is reduced to ten or less. Reduction of Q may be accomplished by adding a resistor 52, which may be 1000 ohms, in parallel with coil 26. Alternatively, a resistor of typically ten ohms may be added in series with coil 26. In some applications, the high resistivity material of conductor 32, which is preferably used, may reduce the Q factor sufficiently to permit stable operation without the use of additional resistors. However, for certain application, a further reduction in Q may be required and a resistor such as resistor 52, will be required.

When high resistance leads 46 and 48 and a high frequency (e.g. greater than 1 MHz for long leads or greater than 10 MHz for short leads) are used, radio frequency attenuation in the leads 46 and 48 will require an extremely sensitive detector 24. To reduce this attenuation, a diode 53 may be added to rectify the coil 26 output voltage. The external circuit capacitances act as a smoothing capacitor, thereby providing a d.c. voltage, which is attenuated much less, to be provided over leads 46 and 48 to detector 24. The signal to noise ratio may be improved when it is possible to modulate the source of the radiation, and add a filter to detector 24.

Figures 3, 4, 5:
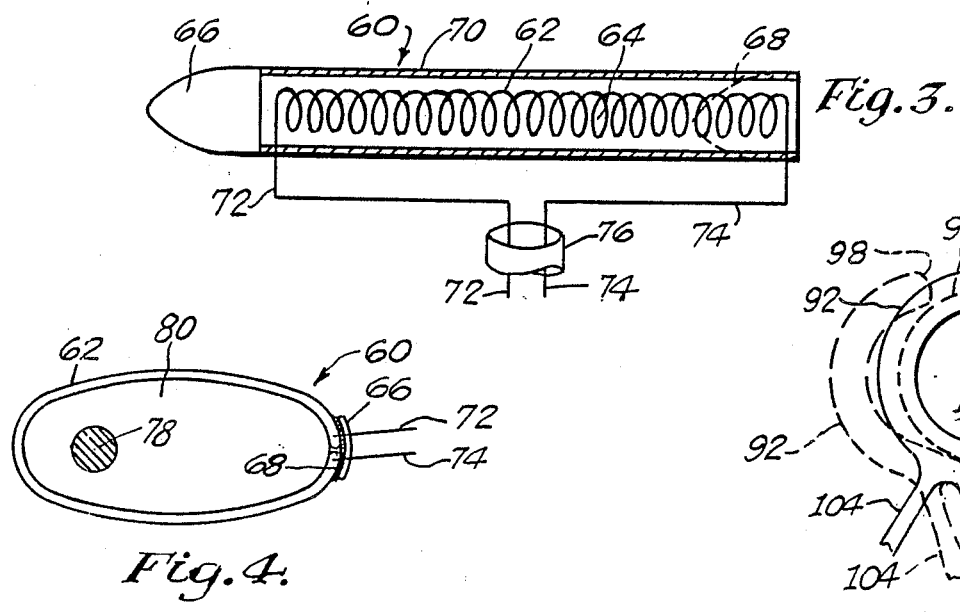
FIG. 3 shows another embodiment of the personal dosimeter device of the subject invention.
FIG. 4 shows a general manner in which the personal dosimeter device, shown in FIG. 3, can be affixed around an object for measuring high frequency current flowing therein.
FIG. 5 shows yet another embodiment of the personal dosimeter device of the subject invention.

Referring now to FIGS. 3 and 4, a belt dosimeter 60 is shown, in which the structure, described in detail above with respect to FIG. 2, is fabricated into a belt arrangement adapted to be strapped around an object, such as the ankle or knee of a person, for use in either FIG. 1 type environment or for use as a personal dosimeter by a person working in a potentially hazardous electromagnetic energy environment. The belt dosimeter 60 device may also be strapped around any other type conductors, where the current therethrough is desired to be measured.

Belt dosimeter 60 includes a high resistivity coil 62 surrounding an air core 64 in the manner described above in respect to FIG. 2. Extending from one end of dosimeter 60 is a portion 66 of a connector, such as the hooks side of hook and loop type fastener, such as Velcro. The other portion 68 of the connector is shown in dash lines as being on the opposite end of coil 62 and may be the loop portion of the hook and loop type fastener. Connector portion 68 may be positioned above the shield material 70 surrounding coil 62 and aligned to mate with portion 66 when the two coil 62 ends are fastened together to form a closed coil 62.

Extending from each end of coil 62 is respective leads 72 and 74, which are adapted to be inserted along a lead shield 76 when portion 66 is affixed to portion 68 of the fastener. Means (not shown) may be including for attaching a shield 76 to the assembled closed loop forming dosimeter 60 when portion 66 is affixed to portion 68. The two portions of the connector 66 and 68 should be arranged so that when portions 66 is affixed to portions 68, leads 72 and 74 are separated from one another by the same spacing as between turns forming coil 62. In order to make coil 62 sufficiently flexible for being formed into a closed loop around a conductor, shield 70 should be a flexible material, such as conductive rubber.

Referring now to FIG. 4, the manner in which belt dosimeter 60 may be affixed around the object 78 is shown. It should be noted that object 78 need not be centered in aperture 80 formed by the coil 62 of dosimeter 60. Further, it should be noted that the aperture 80 need not be circular in shape. By utilizing the high resistivity leads and shielding, as previously discussed, the exact position of conductor 78 within aperture 80 is not critical. However, it should be understood that the length of the coil 62, or its circumference when connected together as in FIGS. 2 and 3, should be less than three times the wavelength of the frequency being measured. Ideally, the circumference of coil 62 should be less than the wavelength of the frequency being measured, but experiments have shown that it is usable with acceptable error up to three times the wavelength of the frequency.

Referring now to FIG. 5, clamp-on ammeter 90 operating according to the principals of the subject invention is shown. Ammeter 90 includes a coil 92 and a pair of leads 94 and 96 extending back from the ends 98 and 100 of coil 92. The ends 98 and 100 should be spaced apart so that the exiting point for leads 94 and 96 are spaced from one another by an amount substantially the same as the distance between adjacent turns on coil 92. Leads 92 and 94 may be buried beneath the flexible shield 99 of coil 92 and extend through a main handle 102 from which they exit and are applied to a detector, such as the high impedance voltage detector 24 shown in FIG. 2. A second handle 104 is also provided and angularly spaced apart from main handle 102. When handle 104 is rotated toward handle 102, the ends 98 and 100 of coil 92 are separated, as shown in the dashed lines, and the conductor to be tested may be inserted into the aperture 106 defined by coil 92. When handle 104 is released, the spring tension of coil 92 repositions dosimeter 92 to the configuration shown by the solid lines of in FIG. 5. Additional springs may be positioned between handles 102 and 104 to assist in the closure of clamp-on ammeter 90.

Referring again to FIG. 1, one may use any of the dosimeters described with respect to FIGS. 2 through 5 to measure the current I flowing through the leg of patient 10. It can be expected that the current I through the leg of patient 10 will manifest the aberrant heating caused by the energy from applicator 12. In order to determine the occurrence of this aberrant heating, a dosimeter 14 is placed at various places along the extremities of person 10. As seen in FIG. 1, dosimeter 14 is placed around the ankle of person 10. Other similar dosimeters may be placed at other places along the legs, arms or neck of person 10 to monitor the aberrant heating.

When aberrant heating is found by noting a high current reading on detector 24, the physician or technician may adjust the position of the limbs, or change the frequency of energy from applicator 12 or change the focal point of the applicator 12, energy. Rather than them using multiple dosimeters, the clamp-on dosimeter 90 shown in FIG. 5 may be moved along each limb to monitor for aberrant heating.

Dosimeter 15 is placed around the abdomen of person 10, either as a belt type device shown in FIG. 3, or as part of applicator 12 itself. Dosimeter 15 is intended to monitor the SAR in the region being treated rather than monitor aberrant heating. Where the reading on detector 24 is too low, it may indicate insufficient energy is being applied or that applicator 12 is not properly focused. If the reading from dosimeter is too high, the energy applied by the applicator 12 should be reduced.

What is claimed is:

1. A current detector for detecting high frequency currents flowing through an object comprising:
    a high resistivity conductor wound in multiple turns around a substantially closed loop non-ferromagnetic core, said loop having an aperture greater than the corresponding dimensions of said object to be measured, and, at any given point along said loop the ratio of said turns spacing to said core cross-sectional area at said point are constant; and
    a shield of a high resistivity material surrounding and electrically separated from said wound conductor.

2. The invention according to claim 1 wherein said shield is selected to eliminate capacitive coupling between said high resistivity conductor said object.

3. The invention according to claim 1 wherein said shield includes a gap around said loop.

4. The invention according to claim 3 wherein said gap extends entirely along said closed loop.

5. The invention according to claim 4 wherein the ratio of the volume resistivity to the thickness of the shield material is in the range of 1000 to 1,000,000 ohms.

6. The invention according to claim 3 wherein the ratio of the volume resistivity to the thickness of the shield material is in the range of 1000 to 1,000,000 ohms.

7. The invention according to claim 2 wherein the ratio of the volume resistivity to the thickness of the shield material is in the range of 1000 to 1,000,000 ohms.

8. The invention according to claim 1 wherein the ratio of the volume resistivity to the thickness of the shield material is in the range of 1000 to 1,000,000 ohms.

9. The invention according to claim 1 wherein said shield material is spaced from said wound high resistivity conductor by an amount to permit usable sensitivity and frequency response.

10. The invention according to claim 9, wherein the ratio of the volume resistivity to the thickness of the shield material is in the range of 1000 to 1,000,000 ohms.

11. The invention according to claim 1 wherein said loop has a circumference of less than three times the wavelength of the frequency of the current being detected.

12. The invention according to claim 1:
    wherein the ends of said wound conductor are coupled through respective high resistivity leads to a high impedance voltage detector; and
    wherein a resistance is coupled to one of said high resistivity leads.

13. The invention according to claim 12 wherein a rectifier is coupled between said wound conductor and said high resistivity leads.

* * * * *